United States Patent [19]

Yuhas

[11] 4,226,889
[45] Oct. 7, 1980

[54] COSMETIC STICK COMPOSITION

[75] Inventor: Edward R. Yuhas, Yonkers, N.Y.

[73] Assignee: Dragoco, Inc., Totowa, N.J.

[21] Appl. No.: 971,113

[22] Filed: Dec. 19, 1978

[51] Int. Cl.² .................... A61K 7/42; A61K 7/44; A61K 31/055; A61K 7/021
[52] U.S. Cl. .................... 424/59; 252/522 A; 424/DIG. 5; 424/DIG. 13; 424/60; 424/63; 424/64; 424/65; 424/67; 424/68; 424/145; 424/347; 424/357; 424/361
[58] Field of Search .................... 424/DIG. 5, 59, 65, 424/60, 64, 63, 358, 357, DIG. 10; 252/522

[56] References Cited

U.S. PATENT DOCUMENTS

| | | | |
|---|---|---|---|
| 2,300,769 | 11/1942 | Berry | 424/DIG. 5 |
| 2,756,178 | 7/1956 | Verblen | 424/DIG. 5 |
| 2,799,613 | 7/1957 | Blödorn | 424/DIG. 5 |
| 2,819,995 | 1/1958 | Wassell | 424/DIG. 5 |
| 2,828,265 | 3/1958 | Van Strien | 424/DIG. 5 |
| 2,838,442 | 6/1958 | McMaster | 424/DIG. 5 |
| 2,857,315 | 10/1958 | Teller | 424/DIG. 5 |
| 2,890,987 | 6/1959 | Hilfer | 424/DIG. 5 |
| 2,948,684 | 8/1960 | Thiele | 424/65 X |
| 2,970,083 | 1/1961 | Bell | 424/DIG. 5 |
| 3,122,481 | 2/1964 | Wotzilka et al. | 424/DIG. 5 |
| 3,252,082 | 6/1966 | Barton | 424/DIG. 5 |
| 3,259,545 | 7/1966 | Teller | 424/DIG. 5 |
| 3,576,776 | 4/1971 | Muszik et al. | 424/DIG. 5 |
| 3,929,986 | 12/1975 | Bouillon et al. | 424/DIG. 5 |
| 3,957,969 | 5/1976 | Fujiyama et al. | 424/DIG. 5 |
| 4,011,311 | 3/1977 | Noomen et al. | 424/DIG. 5 |
| 4,072,742 | 2/1978 | Bouillon et al. | 424/DIG. 5 |

FOREIGN PATENT DOCUMENTS 1230884  5/1971  United Kingdom ............ 424/DIG. 5

*Primary Examiner*—Dale R. Ore
*Attorney, Agent, or Firm*—Kenyon & Kenyon

[57] ABSTRACT

Solid, stick-type cosmetic compositions consist essentially of from about 1 to about 30 parts by weight of sodium stearate, 100 parts by weight of water and an "active" material intended to be applied to the skin. The composition also preferably contains a polyhydroxyl compound, such as a glycol or a polyglycol in an amount of from about 0.5 to about 10 weight percent. The compositions are useful as deodorant sticks, perfume sticks, sun sticks, hand lotion sticks, talc sticks, pigment sticks and insect repellant sticks.

23 Claims, No Drawings

COSMETIC STICK COMPOSITION

The present invention is concerned with stick-type cosmetic compositions. More specifically, the present invention relates to inexpensive stick-type cosmetic compositions.

BACKGROUND

The use of cosmetic preparations in stick form is well known. These preparations have varied from stick-type deodorants and antiperspirants to lipsticks to compressed cosmetic powder sticks. Depending upon the specific application, the vehicle employed in a stick-type cosmetic can vary greatly.

For example, stick-type deodorant compositions typically consist of a bacteriostat or other biologically active compound dispersed in a vehicle comprising an alcohol-based gel containing either ethanol or a glycol such as propylene glycol, as the vehicle base. In either case, gelation is effected by use of a soap, e.g., sodium stearate, as the gelling agent. These stick-type deodorants may also contain small amounts of other additives, such as perfumes, humectants, various surfactants, dyes or other colorants, water, etc. Both types of formulation have left something to be desired. For example, the ethanol in the ethanol-based product is relatively volatile and can evaporate on storage, especially at elevated temperatures. As a consequence, the stick shrinks and becomes mis-shapen and generally useless. The glycol-based deodorant sticks do not suffer from this disadvantage; however, glycols provide a product which is hard and waxy, and thus has an undesirable "feel" and/or little covering power.

Lipsticks and similar cosmetic products, on the other hand, typically employ fats and/or waxes, such as castor oil, carnauba wax, candelia wax, beeswax, and the like. Vehicles of this type are relatively expensive, and in many cases cannot be employed in the formulation of other cosmetic products.

Powder sticks have been formed by compression of the powder; however, such products are generally so hard that it is difficult to deposit sufficient powder when the compressed powder is applied to the skin of the user. As a consequence, various solutions have been proposed, such as reducing the degree of compression, coupled with providing the composition with a separate wrapper or a dry film to prevent "shedding" of the loosely compacted powder. See, e.g., U.S. Pat. No. 3,471,611. In another effort, the use of gums or other materials as adhesive binders have been described in U.S. Pat. No. 3,800,034. Such efforts have not been particularly successful, and by increasing the number of manufacturing steps, necessarily increase cost of manufacture of the product.

DESCRIPTION OF THE INVENTION

It is an object of this invention to provide an improved cosmetic stick composition.

It is a further object of this invention to provide a new, low cost vehicle base for cosmetic stick compositions.

A further object of this invention is to provide a new vehicle capable of use in cosmetic stick compositions having a variety of uses.

Still another object of this invention is to provide a vehicle suitable for use in deodorant sticks, lipsticks, talc sticks and other cosmetic stick applications.

These and other objects of this invention, which will be apparent from the ensuing specification and claims, are achieved by a solid composition consisting essentially of water, sodium stearate and one or more "active" ingredients intended to be deposited on human skin.

The basic vehicle of the composition of this invention is a mixture of water and sodium stearate in proportions sufficient to form a self-supporting solid composition which does not readily deform and yet is not so firm that a hard, waxy composition results which will not leave a deposit of the "active" ingredient on skin to which the composition is applied. In general, suitable products are obtained when the proportion of sodium stearate is in the range of from about 1 to about 30 parts by weight per 100 parts of water. Preferred compositions ordinarily are obtained when the amount of sodium stearate is from about 2 to about 20 parts per 100 parts of water. Of course, the optimum proportion of sodium stearate to water in any particular instance will depend upon the nature of the other ingredients of the cosmetic stick composition. Nonetheless, most useful compositions will have proportions of sodium stearate to water within the above ranges.

The third essential ingredient of the cosmetic stick composition of this invention is an "active ingredient", by which is meant an ingredient which it is desired to deposit on the skin of a human being. Such active ingredients can include biologically active materials such as bacteriostats and fungistats, pigments and dyes or other colorants, perfumes, emollients, ultraviolet absorbers or "sun screens", and talc. Of course, any active ingredient must be stable in the aqueous alkaline environment provided by the sodium stearate-water vehicle. Consequently, antiperspirant materials, such as aluminum chlorohydrate and related materials cannot be employed in the present invention. Depending upon the intended end use of the cosmetic stick composition, the amount of the "active ingredient" can vary from as little as 0.05 weight percent or less up to 50 weight percent or more of the total weight of the composition.

The composition of this invention can be employed to form a deodorant stick composition, wherein the active ingredient is a bacteriostat. Suitable bacteriostats include 2,2'-methylene-bis(3,4,6-trichlorophenol), 2,4,4'-trichloro-2'-hydroxy(diphenyl ether), zinc phenolsulfonate, 2,2'-thiobis(4,6-dichlorophenol), p-chloro-m-xylenol, dichloro-m-xylenol and the like. In such deodorant stick compositions, the proportion of sodium stearate is desirably from about 2 to about 15, and preferably from about 9 to about 12, parts per 100 parts of water. The proportion of bacteriostat is an amount sufficient to act as a deodorant, i.e., to provide a deposit on skin to which the composition is applied which is effective to inhibit the growth of bacteria. Such amounts ordinarily are in the range of from about 0.05 to about 0.5 weight percent, and preferably from about 0.075 to about 0.2 weight percent, of the total composition.

Perfume sticks based upon the stearate-water system can be prepared by including one or more aromatic substances into the composition. These aromatic substances may include natural products such as essential oils, flower oils, natural extracts from resins, gums, balsams, beans, mosses and other plants, and animal fixtures such as ambergris and musk, as well as synthetic aromatic materials. The variety of such materials is too great to list. Suffice it to say that they generally fall into several well known categories, such as the floral, the spicy, the woody, the chypre or mossy, the oriental, the herbal, the leather-tobacco and the aldehydic groups. Men's fragrances can be classified into the citrus, the spice, the leather, the lavender, the fougere, and the woody groups. Typically, fragrance materials are supplied as concentrates which generally contain from about 0.5 to about 20 percent, and more usually contain from about 3 to about 12 percent of one or more fragrance compounds in a solvent such as water or alcohol. In forming a perfume stick composition from such concentrates, the proportion of sodium stearate is from about 5 to about 15, and preferably from about 10 to about 12, parts per 100 parts of water, and the amount of fragrance concentrate is from about 2 to about 8, and preferably from about 3 to about 5, weight percent of the total composition.

Another type of stick-type cosmetic product which may be prepared in accordance with this invention is a sun stick, in which the active ingredient is an ultraviolet absorber such as p-aminobenzoic acid, its salts or its esters, as well as N-substituted derivatives such as p-(dimethylamino) benzoic acid, an anthranilate, a salicylate, esters of cinnamic acid, dihydroxycinnamic acid or trihydroxycinnamic acid, diphenyl-butadiene, stilbene, a napthol sulfonate, a coumarin derivative, a quinine salt, a quinoline derivative, hydroquinone, tannic acid, zinc oxide, dioxybenzone and oxybenzone. In such compositions, the sodium stearate is present in an amount of from about 5 to about 15, and preferably from about 10 to about 12, parts by weight per 100 parts of water, and the ultraviolet absorber or screen is present in an amount of from about 0.5 to about 5 percent, and preferably from about 1 to about 4 percent of the total weight of the composition.

Still another cosmetic stick composition within the scope of this invention is an emollient and lubricating composition wherein the "active ingredient" is a water compatible humectant or emollient composition. Such a composition includes sugar derivatives, for example sucrose and glucose which have been esterified with long chain fatty acids such as stearic acid, e.g., sucrose monostearate, and/or sucrose distearate, and glucose derivatives such as methyl glucoside sesquistearate as well as ethoxylated and propoxylated sugars such as ethoxylated methyl glucose sesquistearate and propoxylated glucose. In such compositions, the sodium stearate is employed in an amount of from about 5 to about 15 parts, and preferably from about 10 to about 12 parts per 100 parts water, and the humectant and/or emollient is employed in an amount of from about 2 to about 10, and preferably from about 4 to about 8 percent of the weight of the total composition.

The compositions of this invention also comprise make-up sticks, in which a solid pigment to be applied as a rouge, lipstick, eye-shadow, eye-liner, etc., is incorporated into the composition as the active ingredient. The pigments include titanium dioxide, zinc oxide, iron oxide and the like, aluminum lake, barium lake, calcium lake, strontium lake, tetrabromofluorescein, tetrabromotetrachlorofluorescein, dibromofluorescein and the like. In such compositions, the amount of sodium stearate is from about 5 to about 15, and preferably from about 9 to about 12 parts per 100 parts of water, and the amount of pigment is from about 1 to about 10 percent, and preferably from about 3 to about 8 percent, based on the total weight of the composition.

A further specific cosmetic formulation embodying the present invention comprises a solid talc stick, in which the "active ingredient" is powdered cosmetic grade talc, which typically has particles whose sizes are about 200 mesh or less, and more specifically are in the range of from about 200 to about 400 mesh (U.S. Standard Series). In such a composition, the amount of sodium stearate can vary from about 1 to about 30, and preferably from about 8 to about 20 parts per 100 parts of water, and the amount of talc can vary from about 10 to about 100, and preferably from about 10 to about 50 parts per 100 parts of water.

It also is within the scope of this invention that two or more active substances can be present. For example, a talc stick can also include a bacteriostat and/or a fungistat for use as a medicated powder stick, for example a foot powder stick, or it can contain a pigment for use as a pigmented talc stick.

Apart from the sodium stearate, water and "active ingredient," the cosmetic stick composition of this invention may contain small amounts of ingredients intended primarily to modify the properties of the stick compositions, and not for deposit on human skin. In particular, it is highly desirable to include relatively small amounts of water compatible polyhydroxyl compound, e.g. glycerine, a glycol or a polyglycol, to modify the physical properties of the composition. Suitable glycols and polyglycols include glycols having at least 2 carbons and preferably from about 3 to about 6 carbons, such as propylene glycol, butylene glycol, and hexylene glycol, and polyglycols such as polyethylene and polypropylene glycols having molecular weights of up to about 25,000, such as dipropylene glycol, and polyethylene glycols having molecular weights in the range of from about 150 to about 25,000 and the like. The glycols and the lower molecular weight polyglycols, i.e., those having molecular weights of below about 10,000 are useful in providing a composition which is somewhat softer, and aid in promoting deposition of the "active" ingredient onto the skin of the user. The higher molecular weight polyglycols, for example a polyethylene glycol sold by Union Carbide Corp as "Carbowax 20M", in contrast can be employed to provide increased hardness. Their use permits the formulation of stick-type cosmetic products containing up to about 95 weight percent water. When employed, the glycol compound comprises from about 0.5 to about 10 weight percent, and preferably from about 1 to about 8 weight percent of the total cosmetic stick composition.

Still other components of the talc stick are odorants and colorants, which are primarily intended to impart a color or fragrance to the stick composition. By the term "odorant", as employed herein, is meant an additive such as a perfume which give the composition a desired odor, as well as an odor mask, which is intended to mask the characteristic odors of other ingredients and thus provide an "unscented" product. By the term "colorant", as employed herein, is meant a dye or other agent employed to impart a particular color to or to mask a particular color of the deodorant stick composition. Ordinarily, such additives will comprise from about 0.1 to about 1 weight percent of the cosmetic stick composition.

Preferred cosmetic stick compositions of this invention generally contain at least 90 weight percent active ingredient, sodium stearate and water, with the balance (10 weight percent or less) being polyhydroxyl compound and odorant or colorant.

The composition of this invention is formed by mixing the ingredients at elevated temperatures sufficient to form a liquid solution or suspension, ordinarily about 70° to about 85° C., pouring the liquid into a mold or dispensing container and allowing it to cool and set. In some cases, a period of several hours or even days may be required before the cosmetic stick composition is completely solidified. It is preferred that the water and sodium stearate, and optionally the other liquid or liquifiable ingredients, be first mixed to form a clear solution, and the solid ingredients such as talc or pigments are then added. The mixture is then partially cooled, at which time volatile components, such as perfume oils, are added, and then final cooling is effected.

The following examples are illustrative.

EXAMPLE 1

Deodorant Stick Formulations

A series of six compositions was prepared containing from 0.5 to 20 parts by weight of sodium stearate, 93 to 73.5 parts by weight of water, 6 parts by weight of propylene glycol, 0.1 part by weight of 2,4,4'-trichloro-2'-hydroxy(diphenyl ether) (THDE), and 0.4 parts by weight of perfume. For each composition, all ingredients but the perfume were heated at 70°-75° C. with stirring until a clear solution was formed. The solution was cooled to 60°-65° C. and the perfume was added. The resulting solution was then poured into a dispensing container and allowed to cool and set. Each of the compositions was then examined for consistency. The results are summarized below.

| Components, wt. % | Deodorant Composition | | | | | |
|---|---|---|---|---|---|---|
| | A | B | C | D | E | F |
| Sodium stearate | 0.5 | 1.0 | 4.0 | 8.5 | 10.0 | 20.0 |
| Water | 93.0 | 92.5 | 89.5 | 85.0 | 83.5 | 73.5 |
| Propylene glycol | 6.0 | 6.0 | 6.0 | 6.0 | 6.0 | 6.0 |
| THDE | 0.1 | 0.1 | 0.1 | 0.1 | 0.1 | 0.1 |
| Perfume | 0.4 | 0.4 | 0.4 | 0.4 | 0.4 | 0.4 |
| Evaluation: | Watery and soft | Watery and soft | Solid, with wet surface | Smooth, hard stick which leaves good deposit on skin | Smooth, hard stick which leaves good deposit on skin | Very hard, waxy "candle" with no "payoff" |

Of the formulations tested, compositions D and E containing 8.5 and 10 percent sodium stearate provided the best balance of properties.

EXAMPLE 2

Deodorant Stick Formulation

A mixture of 8.5 parts by weight of sodium stearate, 6 parts by weight of propylene glycol, and 84 parts by weight of water was heated to 70°-75° C. with constant stirring until a clear solution was formed. The composition was then cooled to 60°-65° C. and 1 part by weight of zinc phenol sulfonate and 0.5 part by weight of perfume were added. The resulting composition was poured into a dispensing container and allowed to cool and set. A firm, hard composition was formed which formed a satisfactory deposit of deodorant when applied to human skin.

EXAMPLE 3

Perfume Stick Formulations

Mixtures of 8.5 parts by weight of sodium stearate, 6 parts by weight of propylene glycol, and a perfume concentrate and water in varying proportions were prepared by heating the sodium stearate, propylene glycol and water at 70°-75° C., with stirring, until a clear solution was formed. The solution was cooled to 65° C. and the perfume concentrate was added. The resulting mixture was then poured into a dispensing container and allowed to cool and set. Each of the compositions was then examined for consistency. The results are summarized below:

| Components, wt. % | Perfume Stick Composition | | | | | |
|---|---|---|---|---|---|---|
| | A | B | C | D | E | F |
| Sodium stearate | 8.5 | 8.5 | 8.5 | 8.5 | 8.5 | 8.5 |
| Propylene glycol | 6.0 | 6.0 | 6.0 | 6.0 | 6.0 | 6.0 |
| Perfume | 2.0 | 4.0 | 6.0 | 8.0 | 10.0 | 15.0 |
| Water | 83.5 | 81.5 | 79.5 | 77.5 | 75.5 | 70.5 |
| Evaluation: | Firm stick with good odor | Same as A | Same as A | Slightly softer stick | Softer stick | Soft stick |

Based upon the foregoing, compositions containing up to about 8 weight percent of perfume concentrate had sufficient physical integrity to be of practical value as a perfume stick.

EXAMPLE 4

Sun Stick Compositions

A mixture of 8.5 parts of sodium stearate, 6.0 parts of propylene glycol and 82.5 or 84.3 parts of water was heated with stirring at 70°-75° C. until a clear solution was obtained and then either 3.0 or 1.2 parts of an ultraviolet absorber or sun screen was added. The resulting mixture was poured into a dispenser tube and allowed to cool and set to form sun stick compositions having good consistency. The various compositions were as follows:

| Components, wt. % | Sun Stick Composition | | | |
|---|---|---|---|---|
| | A | B | C | D |
| Sodium stearate | 8.5 | 8.5 | 8.5 | 8.5 |
| Propylene glycol | 6.0 | 6.0 | 6.0 | 6.0 |

-continued

| Components, | Sun Stick Composition | | | |
|---|---|---|---|---|
| wt. % | A | B | C | D |
| Zinc oxide | 3.0 | — | — | — |
| Dioxybenzone | — | 3.0 | — | — |
| Oxybenzone | — | — | 3.0 | — |
| p-(dimethylamino)-benzoic acid | — | — | — | 1.2 |
| Water | 82.5 | 82.5 | 82.5 | 84.3 |

EXAMPLE 5

Humectant Stick Formulations

Mixtures of 8.5 parts by weight of sodium stearate, 85.5 parts by weight of water and 6 parts by weight of certain sugar derivatives sold as humectants by Croda, Inc. under the designation "Crodesta" or by Amerchol under the designations "Glucam", "Glucate" and "Glucamate", were heated with stirring at 70°–75° C. until a clear solution was formed. Each solution was poured into a dispensing container and alowed to set, to form a humectant stick-type product. The formulations were:

| Components, | Humectant Composition | | | | | |
|---|---|---|---|---|---|---|
| wt. % | A | B | C | D | E | F |
| Sodium stearate | 8.5 | 8.5 | 8.5 | 8.5 | 8.5 | 8.5 |
| Sucrose distearate[1] | 6.0 | — | — | — | — | — |
| Sucrose mono- and distearates[2] | — | 6.0 | — | — | — | — |
| Propoxylated (10 moles) glucose[3] | — | — | 6.0 | — | — | — |
| Propoxylated (20 moles) glucose[4] | — | — | — | 6.0 | — | — |
| Methyl glucoside sesquistearate[5] | — | — | — | — | 6.0 | — |
| Ethoxylated (20 moles) methyl glucose sesqui-stearate[6] | — | — | — | — | — | 6.0 |
| Water | 85.5 | 85.5 | 85.5 | 85.5 | 85.5 | 85.5 |

[1]Sold by Croda, Inc. under the designation Crodesta F 10
[2]Sold by Croda, Inc. under the designation Crodesta F110
[3]Sold by Amerchol under the designation Glucam P 10
[4]Sold by Amerchol under the designation Glucam P 20
[5]Sold by Amerchol under the designation Glucate 55
[6]Sold by Amerchol under the designation Glucamate 55E-20

EXAMPLE 6

Lanolin Stick Formulations

Mixtures of 8.5 parts by weight of sodium stearate, 6.0 parts by weight of propylene glycol, 75.5 parts by weight of water and 10.0 parts by weight of lanolin or commercially available lanolin derivatives were prepared by stirring at 70°–75° C. until a clear solution was obtained, poured into dispensing containers and allowed to cool and set to form lanolin stick formulations useful as solid, stick-form hand creams. The formulations were as follows:

| Components, | Lanolin Composition | | | | | | | | | | | | |
|---|---|---|---|---|---|---|---|---|---|---|---|---|---|
| wt. % | A | B | C | D | E | F | G | H | I | J | K | L | M |
| Sodium stearate | 8.5 | 8.5 | 8.5 | 8.5 | 8.5 | 8.5 | 8.5 | 8.5 | 8.5 | 8.5 | 8.5 | 8.5 | 8.5 |
| Propylene glycol | 6.0 | 6.0 | 6.0 | 6.0 | 6.0 | 6.0 | 6.0 | 6.0 | 6.0 | 6.0 | 6.0 | 6.0 | 6.0 |
| Lanolin, anhyd, USP. | 10.0 | — | — | — | — | — | — | — | — | — | — | — | — |
| Laneto-100[a] | — | 10.0 | — | — | — | — | — | — | — | — | — | — | — |
| Laneto-50[a] | — | — | 10.0 | — | — | — | — | — | — | — | — | — | — |
| Ritachol-5115[a] | — | — | — | 10.0 | — | — | — | — | — | — | — | — | — |
| Super Sat[a] | — | — | — | — | 10.0 | — | — | — | — | — | — | — | — |
| Solulan BP-5[b] | — | — | — | — | — | 10.0 | — | — | — | — | — | — | — |
| Solulan BP 10[b] | — | — | — | — | — | — | 10.0 | — | — | — | — | — | — |
| Solulan C-24[b] | — | — | — | — | — | — | — | 10.0 | — | — | — | — | — |
| Solulan L-575[b] | — | — | — | — | — | — | — | — | 10.0 | — | — | — | — |
| Acetulan[b] | — | — | — | — | — | — | — | — | — | 10.0 | — | — | — |
| Ricilan-B[b] | — | — | — | — | — | — | — | — | — | — | 10.0 | — | — |
| Ricilan-C[b] | — | — | — | — | — | — | — | — | — | — | — | 10.0 | — |
| Viscolan[b] | — | — | — | — | — | — | — | — | — | — | — | — | 10.0 |
| Water | 75.5 | 75.5 | 75.5 | 75.5 | 75.5 | 75.5 | 75.5 | 75.5 | 75.5 | 75.5 | 75.5 | 75.5 | 75.5 |

[a]Laneto, Super Sat and Riachol all are products of Rita Chemical Co.
[b]Acetulan, Solulan, Ricilan and Viscolan all are products of Americol.

All of the compositions were firm solids which were useful as "hand lotions", although compositions A and E had a slightly tacky feel which was not evidenced by the other lanolin stick composition.

EXAMPLE 7

Talc Stick Formulations

A series of seven compositions was prepared by mixing sodium stearate, water, propylene glycol and 2,4,4'-trichloro-2'-hydroxy(dephenyl ether) (THDE) and stirring at 70° to 75° C. The composition was removed from the heat, and talc was stirred in to form a uniform slurry. The slurry was cooled to 60° to 65° C. and perfume was added. The resulting composition were poured into stick-type dispensers and allowed to cool and set. The resulting compositions were then evaluated for physical appearance, form and efficacy in depositing talc. The results are summarized as follows:

| | Talc Stick Composition | | | | | | |
|---|---|---|---|---|---|---|---|
| Component, wt. %: | A | B | C | D | E | F | G |
| Talc | 1.0 | 5.0 | 10.0 | 20.0 | 30.0 | 40.0 | 50.0 |
| Sodium stearate | 8.5 | 8.5 | 8.5 | 8.5 | 8.5 | 8.5 | 8.5 |
| Water | 84.0 | 80.0 | 75.0 | 65.0 | 55.0 | 45.0 | 35.0 |
| Propylene glycol | 6.0 | 6.0 | 6.0 | 6.0 | 6.0 | 6.0 | 6.0 |
| THDE | 0.1 | 0.1 | 0.1 | 0.1 | 0.1 | 0.1 | 0.1 |
| Perfume | 0.4 | 0.4 | 0.4 | 0.4 | 0.4 | 0.4 | 0.4 |

The compositions all were firm solids. However, compositions A and B contained insufficient talc to form a satisfactory deposit when applied to skin. Composition G was too stiff for practical use. Compositions C, D, E and F all provided an adequate deposit of talc when applied to skin. Furthermore, the talc deposit was quite adherent and difficult to rub off the skin. Compositions E and F provided the best balance of properties.

EXAMPLE 8

Talc Stick Formulations

Mixtures of 8.5 parts of sodium stearate, 6.0 parts of a polyethylene glycol, and 55.5 parts of water were stirred at 70°–75° C. The compositions were removed from the heat and talc was stirred in to form a slurry. The resulting compositions were poured into stick-type dispensers and allowed to cool and sit to firm solid talc stick.

| Components, wt. %: | Talc Stick Compositions | | | |
|---|---|---|---|---|
| | A | B | C | D |
| Sodium stearate | 8.5 | 8.5 | 8.5 | 8.5 |
| Polyethylene glycol-200[1] | 6.0 | — | — | — |
| Polyethylene glycol-1000[2] | — | 6.0 | — | — |
| Polyethylene glycol-4000[3] | — | — | 6.0 | — |
| Polyethylene glycol-6000[4] | — | — | — | 6.0 |
| Talc | 30.0 | 30.0 | 30.0 | 30.0 |
| Water | 55.5 | 55.5 | 55.5 | 55.5 |

[1] Sold by Union Carbide Corp. as Carbowax 200
[2] Sold by Union Carbide Corp. as Carbowax 1000
[3] Sold by Union Carbide Corp. as Carbowax 4000
[4] Sold by Union Carbide Corp. as Carbowax 6000

EXAMPLE 9

Talc Stick Formulation

Talc sticks containing 8.5 parts by weight sodium stearate, 6.0 parts by weight of polyethylene glycol having a molecular weight of about 6000–7500 (Carbowax 6000), from 10 to 45 parts talc and from 75.5 parts to 40.5 parts water were prepared by procedures similar to those described in Example 1.

| Components, wt. %: | Talc Stick Formulation | | | | |
|---|---|---|---|---|---|
| | A | B | C | D | E |
| Sodium stearate | 8.5 | 8.5 | 8.5 | 8.5 | 8.5 |
| "Carbowax 6000" | 6.0 | 6.0 | 6.0 | 6.0 | 6.0 |
| Talc | 10.0 | 20.0 | 30.0 | 40.0 | 45.0 |
| Water | 75.5 | 65.5 | 55.5 | 45.5 | 40.5 |

All talc sticks were solid and firm.

EXAMPLE 10

Pigment Stick Formulations

Employing procedures similar to those described in Example 8, except that brown iron oxide powdered pigment was substituted for or added with talc, three pigment sticks were prepared.

| Components, wt. %: | Pigment Stick Composition | | |
|---|---|---|---|
| | A | B | C |
| Sodium stearate | 12.5 | 12.0 | 8.5 |
| "Carbowax 4000" | 6.0 | 6.0 | — |
| "Carbowax 6000" | — | — | 6.0 |
| Talc | 30.0 | 30.0 | — |
| Pigment | 10.0 | 5.0 | 5.0 |
| Water | 41.5 | 47.0 | 80.5 |

All compositions were solid, dry and left a good deposit pigment when applied to human skin, and were useful as "make up" sticks. The Composition C, containing no talc was somewhat smoother in feel.

EXAMPLE 11

Evaluation of Stearates

A series of mixtures containing 8.5 parts by weight of a stearate, 6.0 parts of propylene glycol, and 85.5 parts of water was prepared by heating with stirring at 70°–75° C. to form a clear solution, pouring into a stick-type dispenser, and cooling to allow the composition to set. The compositions were:

| Components, wt. %: | Stearate Composition | | | | |
|---|---|---|---|---|---|
| | A | B | C | D | E |
| Sodium stearate | 8.5 | — | — | — | — |
| Lithium stearate | — | 8.5 | — | — | — |
| Magnesium stearate | — | — | 8.5 | — | — |
| Zinc stearate | — | — | — | 8.5 | — |
| Aluminum stearate | — | — | — | — | 8.5 |
| Propylene glycol | 6.0 | 6.0 | 6.0 | 6.0 | 6.0 |
| Water | 85.5 | 85.5 | 85.5 | 85.5 | 85.5 |

Of the compositions, all but composition A were extremely soft and totally unsuitable for use as a stick-type cosmetic applicator.

EXAMPLE 12

Evaluation of Glycolic Additives

A series of formulations containing 8.5 parts by weight of sodium stearate, 85.5 parts by weight of a glycolic compound was prepared by procedures described in Example 11. All formed firm solid sticks capable of use in a stick-type cosmetic product.

| Components, wt. % | Composition | | | | | | | | |
|---|---|---|---|---|---|---|---|---|---|
| | A | B | C | D | E | F | G | H | I |
| Sodium stearate | 8.5 | 8.5 | 8.5 | 8.5 | 8.5 | 8.5 | 8.5 | 8.5 | 8.5 |
| Glycerine | 6.0 | — | — | — | — | — | — | — | — |
| Butylene glycol | — | 6.0 | — | — | — | — | — | — | — |
| Hexylene glycol | — | — | 6.0 | — | — | — | — | — | — |
| Triethylene glycol | — | — | — | 6.0 | — | — | — | — | — |
| Dipropylene glycol | — | — | — | — | 6.0 | — | — | — | — |
| Polyethylene[1] glycol-200 | — | — | — | — | — | 6.0 | — | — | — |
| Polyethylene[2] glycol-1000 | — | — | — | — | — | — | 6.0 | — | — |
| Polyethylene[3] glycol-4000 | — | — | — | — | — | — | — | 6.0 | — |
| Polyethylene[4] glycol-6000 | — | — | — | — | — | — | — | — | 6.0 |

-continued

| Components, wt. % | Composition | | | | | | | | |
|---|---|---|---|---|---|---|---|---|---|
| | A | B | C | D | E | F | G | H | I |
| Water | 85.5 | 85.5 | 85.5 | 85.5 | 85.5 | 85.5 | 85.5 | 85.5 | 85.5 |

(1)"Carbowax 200"
(2)"Carbowax 1000"
(3)"Carbowax 4000"
(4)"Carbowax 6000"

Similar results were obtained when the glycolic compound was replaced by 6.0 parts by weight of a high molecular weight alcoholic product sold by Union Carbide Corp. under the general designation "Ucon". Specific products which were employed to form solid stick-type compositions were Ucon LO 500, Ucon 50-HB-260, Ucon 50-HB-660, Ucon 50-HB-5100, Ucon LB-1145 and Ucon LB-1715.

EXAMPLE 13

A series of mixtures of from 2 to 8.5 weight percent sodium stearate, from 81.5 to 96 weight percent water and from 2 to 10 weight percent Carbowax 20 M, a polyethylene glycol having a molecular weight in the range of about 15,000 to 20,000 formed by reaction of 2 moles of Carbowax 6000 with an epoxide, and sold by Union Carbide Corp., was prepared and formed into solid sticks by the procedures described in Example 11. In all cases, firm, solid products capable of use in cosmetic stick-type formulation were obtained.

| Experiment | Composition, weight % | | | |
|---|---|---|---|---|
| | Sodium Stearate | "Carbowax 20 M" | Water | Comment |
| A-1 | 2.0 | 2.0 | 96.0 | Wet, slightly soft solid |
| A-2 | 2.0 | 3.0 | 95.0 | Wet, slightly soft solid |
| A-3 | 2.0 | 4.0 | 94.0 | Wet, slightly soft solid |
| A-4 | 2.0 | 5.0 | 93.0 | Wet, slightly soft solid |
| B-1 | 3.0 | 2.0 | 95.0 | Slightly soft solid |
| B-2 | 3.0 | 3.0 | 94.0 | Slightly soft solid |
| B-3 | 3.0 | 4.0 | 93.0 | Slightly soft solid |
| C-1 | 4.0 | 2.0 | 94.0 | Slightly soft solid |
| C-2 | 4.0 | 3.0 | 93.0 | Slightly soft solid |
| C-3 | 4.0 | 4.0 | 92.0 | Slightly soft solid |
| D-1 | 6.0 | 2.0 | 92.0 | Slightly soft solid |
| E-1 | 8.5 | 0.5 | 91.0 | Slightly hard solid |
| E-2 | 8.5 | 1.0 | 90.5 | Slightly hard solid |
| E-3 | 8.5 | 2.0 | 89.5 | Slightly hard solid |
| E-4 | 8.5 | 4.0 | 87.5 | Slightly hard solid |
| E-5 | 8.5 | 6.0 | 85.5 | Slightly hard solid |
| E-6 | 8.5 | 8.0 | 83.5 | Slightly hard solid |
| E-7 | 8.5 | 10.0 | 81.5 | Slightly hard solid |

From the foregoing, it can be seen that the use of Carbowax 20 M enables the formulation of compositions capable as use as vehicles for solid stick-type cosmetic preparations containing as much as 95 to 96 weight percent water, and as little as 2 weight percent of sodium stearate and the Carbowax 20 M. Compositions having only 2 percent sodium stearate, although slightly soft solids, did have a wet feel which might be undesirable in some applications. This wet feel was eliminated on increasing the sodium stearate content to at least about 3 weight percent. With further increases in the amount of sodium stearate the hardness of the composition increased. At each level of sodium stearate tested, variations in the amount of Carbowax did not appear to materially affect the properties of the product.

The foregoing examples are merely illustrations of the type of cosmetic product which can be made employing the sodium stearate-water vehicle of this invention. Still other cosmetic products will be apparent to those of ordinary skill in the art. For example, stick type insect repellants can be employed by incorporating an insect repellant compound as the active ingredient.

What is claimed is:

1. A cosmetic stick-type composition consisting essentially of:
   (1) an aqueous sodium stearate-water vehicle formed of:
      (a) 100 parts by weight of water; and
      (b) from about 1 to about 30 parts by weight of sodium stearate; and
   (2) from about 0.05 to about 50 weight percent, based upon the total weight of the composition, of at least one cosmetic active ingredient intended to be deposited on human skin, which ingredient is stable in the aqueous alkaline environment provided by said sodium stearate-water vehicle.

2. A composition according to claim 1 wherein the amount of sodium stearate is from about 2 to about 20 parts by weight.

3. A composition according to claim 1 wherein said active ingredient is selected from the group consisting of bacteriostats, fungistats, pigments, dyes, perfumes, emollients, humectants, ultraviolet absorbers, talc and insect repellants.

4. A deodorant stick composition according to claim 1 wherein said active is a bacteriostat in an amount of from 0.05 to about 0.5 weight percent of the total composition, and the amount of sodium stearate is from about 5 to about 15 parts by weight.

5. A deodorant stick composition according to claim 4 wherein the amount of sodium stearate is from about 9 to about 12 parts by weight and the amount of bacteriostat is from about 0.075 to about 0.2 weight percent of the total composition.

6. A perfume stick composition according to claim 1 containing from about 5 to about 15 parts by weight of sodium stearate and from about 2 to about 8 weight percent of a perfume concentrate.

7. A sun stick composition according to claim 1 containing from about 5 to about 15 parts by weight of sodium stearate and from about 0.5 to about 5 weight percent of an ultraviolet absorber.

8. An emollient-humectant stick composition according to claim 1 containing from about 5 to about 15 parts by weight of sodium stearate and from about 2 to about 10 weight percent of an emollient or humectant.

9. A make-up stick composition according to claim 1 containing from about 5 to about 15 parts by weight of sodium stearate and from about 1 to about 10 weight percent of a pigment.

10. A talc stick composition according to claim 1 containing from about 1 to about 30 parts by weight of sodium stearate and from about 10 to about 100 parts by weight of talc per 100 parts water.

11. A talc stick composition according to claim 10 containing from about 8 to about 20 parts by weight of sodium stearate and from about 10 to about 50 parts of talc.

12. A hand lotion stick composition according to claim 1 containing from about 5 to about 15 parts of sodium stearate and from about 5 to about 15 weight percent of lanolin or a lanolin derivative.

13. A cosmetic stick composition according to claim 1 additionally including a polyhydroxyl compound in an amount of from about 0.5 to about 10 weight percent of the total composition.

14. A cosmetic stick composition according to claim 2 additionally including polyhydroxyl compound in an amount of from about 1 to about 8 weight percent of the total composition.

15. A deodorant stick composition according to claim 13 wherein said active is a bacteriostat in an amount of from 0.05 to about 0.5 weight percent of the total composition, and the amount of sodium stearate is from about 2 to about 15 parts by weight.

16. A deodorant stick composition according to claim 15 wherein the amount of sodium stearate is from about 9 to about 12 parts by weight and the amount of bacteriostat is from about 0.075 to about 0.2 weight percent of the total composition.

17. A perfume stick composition according to claim 12 containing from about 5 to about 15 parts by weight of sodium stearate and from about 2 to about 8 weight percent of a fragrance concentrate.

18. A sun stick composition according to claim 13 containing from about 5 to about 15 parts by weight of sodium stearate and from about 0.5 to about 5 weight percent of an ultraviolet absorber.

19. An emollient-humectant stick composition according to claim 13 containing from about 5 to about 15 parts by weight of sodium stearate and from about 2 to about 10 weight percent of an emollient or humectant.

20. A make-up stick composition according to claim 13 containing from about 5 to about 15 parts by weight of sodium stearate and from about 1 to about 10 weight percent of a pigment.

21. A talc stick composition according to claim 13 containing from about 1 to about 30 parts by weight of sodium stearate and from about 10 to 100 parts by weight of talc per 100 parts water.

22. A talc stick composition according to claim 21 containing from about 8 to about 20 parts by weight of sodium stearate and from about 10 to about 50 parts of talc.

23. A hand lotion stick composition according to claim 13 containing from about 5 to about 15 parts by weight of sodium stearate and from about 5 to about 15 weight percent of lanolin or a lanolin derivative.

* * * * *